United States Patent [19]

Munnerlyn

[11] Patent Number: 4,561,436

[45] Date of Patent: Dec. 31, 1985

[54] OPTICAL SYSTEM FOR SURGICAL OPHTHALMIC LASER INSTRUMENT

[75] Inventor: Charles R. Munnerlyn, Sunnyvale, Calif.

[73] Assignee: Cooper LaserSonics, Inc., Santa Clara, Calif.

[21] Appl. No.: 546,397

[22] Filed: Oct. 28, 1983

[51] Int. Cl.⁴ .............................................. A61B 17/36
[52] U.S. Cl. ................................. 128/303.1; 128/395; 219/121 LQ; 219/121 LS; 350/171
[58] Field of Search ...................... 128/303.1, 395–398; 219/121 LP, 121 LQ, 121 LR, 121 LS; 350/171

[56] References Cited

U.S. PATENT DOCUMENTS

| | | | |
|---|---|---|---|
| 3,710,798 | 1/1973 | Bredemeier | 128/303.1 |
| 3,796,220 | 3/1974 | Bredemeier | 128/303.1 |
| 3,828,788 | 8/1974 | Krasnov et al. | 128/303.1 |
| 4,123,143 | 10/1978 | Yachin et al. | 128/303.1 X |
| 4,362,361 | 12/1982 | Campbell et al. | 350/171 |
| 4,409,979 | 10/1983 | Roussel et al. | 128/303.1 |

OTHER PUBLICATIONS

"Commercial Ophthalmic YAG Lasers" by Stephen L. Trokel, from YAG Laser Ophthalmic YAG Lasers, published Feb. 1983, by Appleton, Century, and Crofts.
"Ophthalmic Neodymium: YAG Lasers" by Richard H. Keates, M.D.; Steven Fry, Ph.D.; and William J. Link, Ph.D., Sep. 1982.
"Nikon Zoom-Photo Slit-Lamp Microscope FS-2", a brochure by Nippon Kogaku K.K.

Primary Examiner—Lee S. Cohen
Attorney, Agent, or Firm—C. Michael Zimmerman

[57] ABSTRACT

An optical system for a surgical ophthalmic instrument 10 using a YAG laser reduces the size of the components and facilitates their combination with a binocular microscope 11. A parallel plate beam splitter 22 splits a beam 21 from a visible light He-Ne laser 20 into equal and separated He-Ne beams 21a and 21b. A pair of expanders 27 and 37 diverge the He-Ne beams and a beam 30 from the YAG laser 15. The diverging beams are combined on a coincident optical path, which is collimated and coincided with the optical path of microscope 11 between its binocular head 42 and objective 43. There, a mirror 50 coated to reflect the YAG laser light also has a pair of spaced-apart regions 51a and 51b with a second coating to reflect both the He-Ne beams 21a and 21b so that all laser light converges on the patient's eye. The central mirror region 52 is transparent to visible light so that most of the light reflected from the patient's eye is visible to the surgeon. The lasers and other components are mounted on an optical plate 25 secured to a lower support 12 of microscope 11 where controls are convenient and accuracy is assured.

17 Claims, 5 Drawing Figures

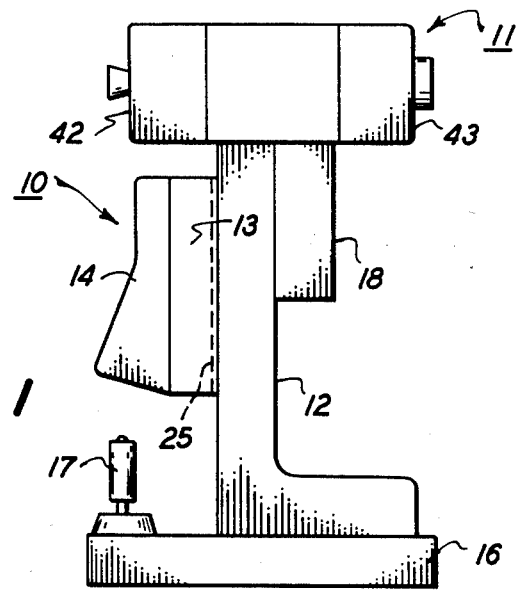
FIG. 1
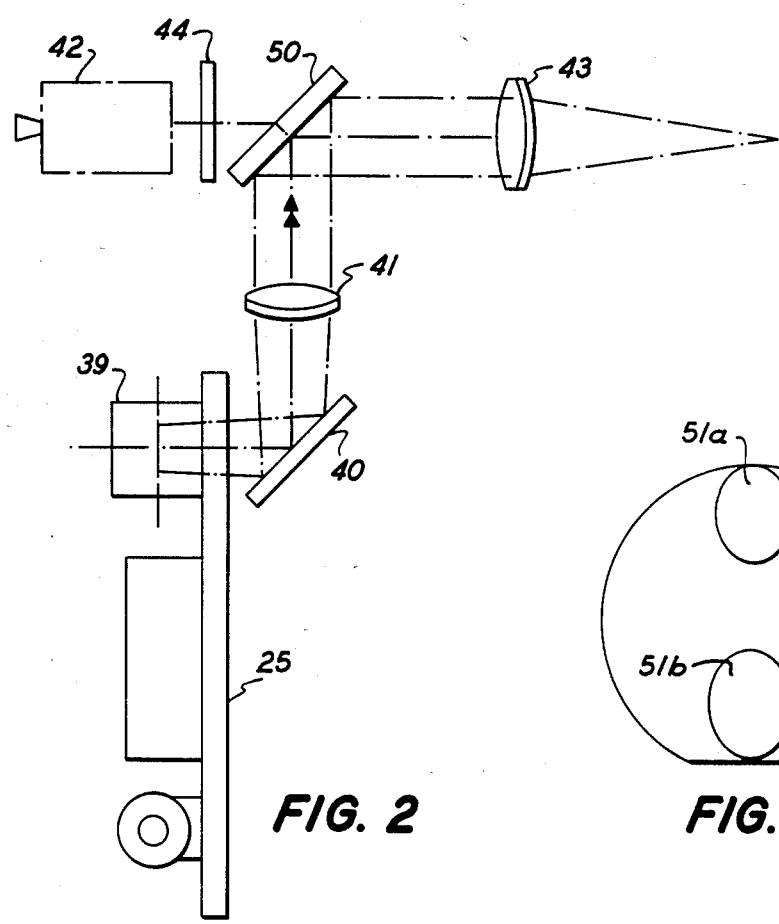
FIG. 2
FIG. 5

4,561,436

OPTICAL SYSTEM FOR SURGICAL OPHTHALMIC LASER INSTRUMENT

BACKGROUND

The medical optics art has suggested several instruments for ophthalmic surgery, and particularly noninvasive surgery using a YAG laser (Pulsed Neodymium: Yitrium-Aluminum-Garnet). The surgical YAG laser beam is first expanded and then converged on the eye so that when the beam concentrates at a focal point within the eye it vaporizes tissue at that point. A succession of carefully positioned laser pulses can destroy tissue within the eye and accomplish some surgical procedures noninvasively.

For aiming and delivering a surgical laser pulse precisely, instruments use a binocular microscope and visible beams from a laser such as a Helium-Neon (He-Ne) laser converging on a focal point coincident with the focal point of the surgical laser beam. While viewing the eye through the microscope, the surgeon can fix the exact location of the focal point for the visible beams and can then deliver a surgically effective pulse at the predetermined point. It is important to locate the focal point of the surgical laser beam accurately in three dimensions to within fractions of a millimeter, and this requires an optical system that can make the focal point of the visible beams clearly viewable and accurately coincident with the surgical laser beam.

I have devised an optical system for a surgical ophthalmic laser instrument that uses light more efficiently, allowing the optical system to be more compact and more accurately combined with the microscope. My system also accurately holds a precise adjustment in the coincidence of the focal points of visible and surgical beams. It results in a compact, sturdy, accurate, and reliable instrument that reduces the chances for error to help and protect both the surgeon and the patient.

SUMMARY OF THE INVENTION

My optical system applies to a surgical ophthalmic laser instrument that includes a binocular microscope and a surgical laser and visible light laser producing substantially different wave lengths of energy. A parallel plate beam splitter receives a beam from the visible laser, and a half-reflective coating on one side and a full reflective coating on the other side cooperate to divide the visible beam into a pair of separated visible beams. A pair of expanders respectively diverge the visible beams and the surgical laser beam, and the diverging beams from each laser combine on a coincident optical path. After divergence, light traveling on the coincident optical path is collimated and directed to a mirror arranged on the optical path of the microscope between its binocular portion and its objective portion. The mirror has a first coating that reflects substantially all of the surgical laser beam and is transparent to visible light, and spaced-apart regions of the mirror have a second coating that reflects substantially all of both the pair of visible beams and the surgical laser beam. I arrange the coatings and the mirror for: (a) directing the pair of visible beams and the surgical laser beam through the objective portion of the microscope to converge on the eye of the patient, (b) transmitting visible light reflected from the patient's eye through the first coating to be viewable with the binocular portion of the microscope, and (c) not transmitting any surgical laser light through the mirror to the binocular portion of the microscope.

My system uses the available visible light effectively enough so that the visible laser can be made smaller, allowing both lasers to be mounted compactly on an optical plate along with the parallel plate beam splitter, the beam expanders, and the beam-combining means. The optical plate in turn can be mounted on a movable support for the microscope so that the optical components are mounted below and move with the microscope to simplify and secure the accuracy of the system.

DRAWINGS

FIG. 1 is a schematic, side elevational view of a surgical ophthalmic laser instrument having a preferred embodiment of my optical system;

FIG. 2 is a partially schematic view of my optical system as applied to the instrument of FIG. 1;

FIG. 5 is a plan view of a preferred mirror for combining the coincident optical paths of the surgical and visible beams with the optical path of the microscope.

DETAILED DESCRIPTION

FIG. 1 schematically shows how my optical system for a surgical ophthalmic laser instrument 10 combines with a binocular microscope 11. My optical system applies to any combination of surgical laser and visible light laser producing substantially different wave lengths of energy, but usually the surgical laser produces energy outside the visible spectrum in the infrared or ultraviolet regions. A laser producing visible light allows the surgeon to view the aiming of a pulse of energy from the surgical laser, and my optical system is arranged to accommodate both a visible aiming light and the surgical energy at a substantially different frequency.

For simplicity, the preferred embodiment of my optical system described below assumes that the surgical laser is a YAG laser and the visible light laser is a He-Ne laser. This is a popular combination of lasers for noninvasive eye surgery. However, other surgical lasers and other visible light lasers can be substituted for the YAG and He-Ne lasers described for instrument 10, so long as the surgical and visible light lasers produce energy at substantially different wave lengths. The advantages my optical system brings to instrument 10 are explained after the following description of the optical system components and their interaction as applied to a YAG laser 15 and a He-Ne laser 20.

Figure 3:
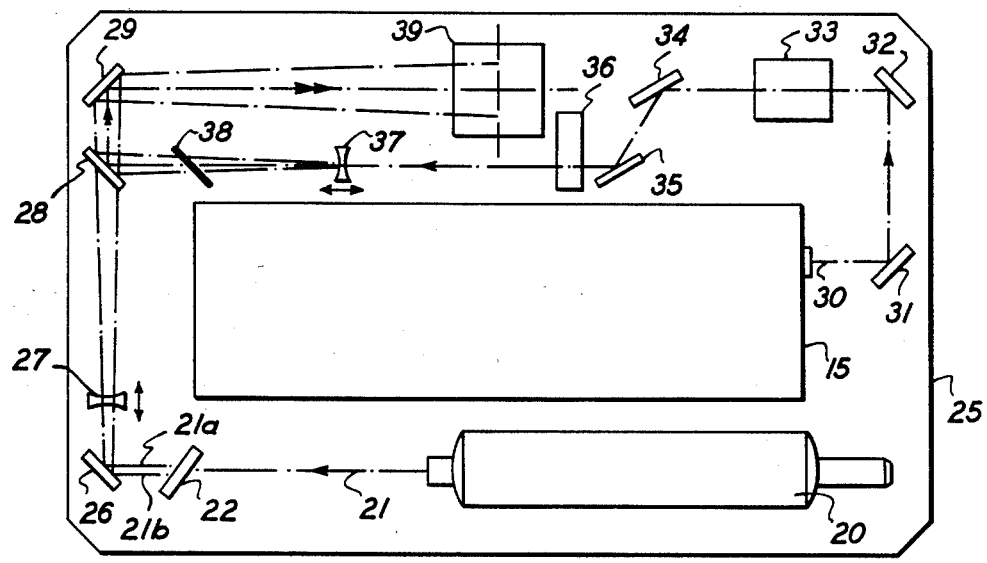
FIG. 3 is a plan view of a preferred embodiment of an optical plate used in the system of FIGS. 1 and 2.
Figure 4:
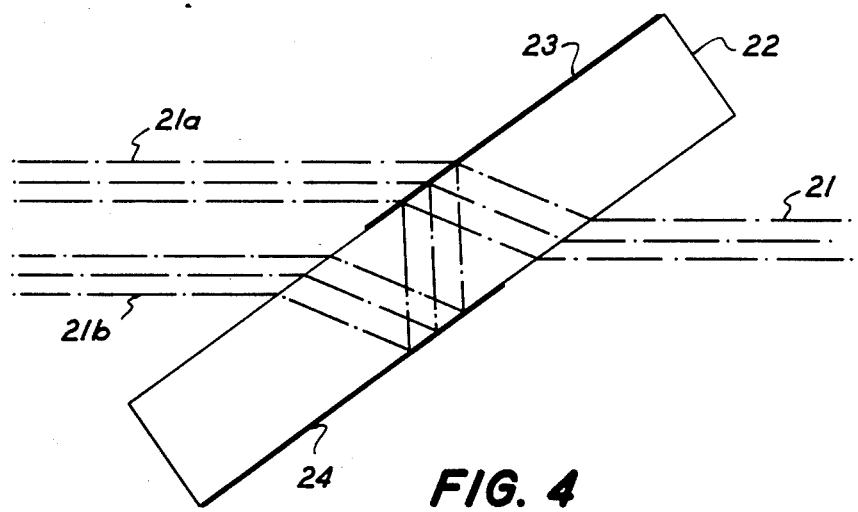
FIG. 4 is a schematic view of a parallel plate beam splitter used in my optical system for dividing a visible beam into a pair of equal and spaced beams.

Lasers 15 and 20 are each mounted on optical plate 25 along with other components that prepare beams from the two lasers for introduction into microscope 11. The components include a parallel plate beam splitter 22, enlarged in FIG. 4, that divides beam 21 from He-Ne laser 20 into a pair of equal and separate beams 21a and 21b. Beam 21 passes through plate 22 and is divided into two equal beams by half-reflective coating 23. One of these beams 21a passes through coating 23, and the other reflects back through plate 22 to full reflective coating 24 that directs beam 21b out of plate 22 where it is spaced from and parallel with beam 21a. He-Ne beam 21 is preferably linearly polarized, and parallel plate 22 is preferably set at Brewster's angle to beam 21 to avoid unwanted surface reflections.

Mirror 26 directs the equal, separated, and parallel He-Ne beams 21a and 21b to an expander 27 that diverges these beams. A dichroic mirror 28 that is transparent to He-Ne light transmits the diverging He-Ne beams 21a and 21b.

Mirrors 31 and 32 direct YAG laser beam 30 through an attenuator 33, and mirrors 34 and 35 direct beam 30 through a beam sensor 36 to an expander 37. Beyond expander 37, YAG beam 30 diverges, passes through a safety stop shutter 38, and is reflected from dichroic mirror 28 to follow a path thereafter coincident with diverging He-Ne beams 21a and 21b.

Mirror 29 directs the coincident optical path of the He-Ne beams and the YAG beam to exit reflector 39 that directs the coincident path through optical plate 25 to reflector 40 as shown in FIG. 2. Reflector 40 is preferably tiltable by small angles for precisely aiming the focal point in the X,Y plane within the patient's eye after coarse adjustment of microscope 11.

From reflector 40, the coincident optical path proceeds upward through collimator 41, and the collimated beams are incident on a mirror 50. Mirror 50 is arranged on the optical path of microscope 11 in a region between binocular portion 42 and objective portion 43 where light is collimated. It directs the collimated light of the YAG and He-Ne beams through objective 43 to converge on the eye of a patient. A safety filter 44 ensures that YAG light cannot enter binocular head 42.

Mirror 50 has a pair of spaced-apart reflective regions 51a and 51 b that are preferably elliptical in shape as shown in FIG. 5. Mirror regions 51a and 51b are preferably arranged at the top and bottom of mirror 50 where He-Ne beams 21a and 21b are preferably incident. This makes the He-Ne beams converge on the eye of the patient from upper and lower extremities of the coincident beam path. The elliptical shape of regions 51a and 51b is suitable for receiving circular cross-sectional He-Ne beams 21a and 21b, and regions 51a and 51b are larger than the incidence area of He-Ne beams 21a and 21b to allow for small angular movement from precision aiming adjustment by reflector 40.

The remaining region 52 of mirror 50 outside of He-Ne beam regions 51a and 51b reflects the YAG beam and is transparent to visible light, including He-Ne light. This lets the surgeon observe light reflected from the eye of the patient through binocular head 42. Arranging He-Ne beam reflecting regions 51a and 51b at top and bottom regions of mirror 50 allows binocular head 42 to view only transparent region 52, which makes the visible light fully available to the surgeon.

My preferred way of coating mirror 50 to accomplish these desired results is to apply a first coating over the entire surface of mirror 50, including regions 52 and 51a and 51b. The first coating is chosen to reflect substantially all YAG light and to be substantially transparent to visible light, including He-Ne light. Then by masking region 52, a second coating applied to regions 51a and 51b is fully reflective of He-Ne light.

I prefer that the second coating in He-Ne beam regions 51a and 51b be made very thin, and preferably only about 500 angstrom units thick so as to be substantially thinner than a quarter-wave length of the YAG light. This avoids interference and the resulting degradation that would otherwise occur between portions of the YAG beam reflected from different region levels of mirror 50. Some metallic coatings can be made as thin as 500 angstrom units, and I prefer a gold coating.

The second coating in regions 51a and 51b could also avoid interference in the YAG beam by being as thick as one-half wave length of YAG light, but this would form a larger discontinuity at the edges of regions 51a and 51b. Such a discontinuity scatters light and somewhat degrades the YAG beam. So the preferred solution is a reflective coating made as thin as possible in regions 51a and 51b to reduce the degradation from the edges of the coatings and to be thin enough to avoid any substantial interference degradation.

For surgical lasers other than YAG lasers producing energy at different wave lengths, coating thicknesses and strategies can vary. For whatever wave lengths are involved, the objective is to minimize interference degradation and scattering of light from coating edge discontinuities.

Prior art systems using an undivided dichroic mirror to direct He-Ne and YAG beams to the patient's eye waste 75% of the He-Ne light. For a dichroic mirror to be both reflective of visible light and transparent to visible light requires loss of about half the energy of each incidence. Half of the He-Ne beam is lost to transmission on the reflection enroute to the patient's eye, and half of the return light from the patient's eye is lost to reflection on the transmission to the binocular head, leaving only 25% visible to the surgeon.

My system with its multi-region mirror 50 effectively uses most of the available light. Regions 51a and 51b fully reflect the He-Ne beams toward the patient's eye, and He-Ne light and other visible light reflected from the patient's eye is nearly all visible to the surgeon because it can pass through mirror region 52 that is transparent to visible light. Binocular microscope head 42, with its side-by-side lenses, views only light passing through region 52 of mirror 50.

One effect of this is that the He-Ne laser in my optical system can be smaller and produce less He-Ne light energy. This not only makes the He-Ne laser lightweight, compact, and inexpensive, but it also reduces the He-Ne light energy that must be converged on the patient's eye to produce enough reflection to be adequately visible to the surgeon. The small size and weight of the He-Ne laser required facilitates integrating my optical system 10 into microscope 11 as shown schematically in FIG. 1.

Optical plate 25 preferably mounts directly on lower support 12 for microscope 11 as schematically shown in FIG. 1 where housing 13 contains optical plate 25 and its optical components. A control panel housing 14 can then be conveniently arranged in front of optics housing 13 to make the necessary controls and indications conveniently available to the surgeon.

Microscope support 12 moves on base 16 in a generally known way for aiming microscope 11, and joystick 17 accomplishes this. With optics plate 25 secured directly to microscope support 12, all the optical components move directly with the microscope 11 to ensure mechanical alignment. This arrangement also disposes the added weight of the optical components below microscope 11 where they do not impair balance and movement. It also avoids alignment inaccuracies that are inherent in articulated arms between optical components fixed in place near a movable microscope. The preferred mounting of the optical system on microscope support 12 also is convenient for directing the coincident optical paths of the laser beams to the optical path of the microscope via a housing 18.

My parallel plate beam splitter 22 efficiently divides He-Ne beam 21 into a pair of beams 21a and 21b with little loss of energy. Separated beams 21a and 21b also cooperate effectively with multi-region dichroic mirror 50 in converging He-Ne beams on the patient's eye and making the result visible to the surgeon.

Adjustment of the coincidence of the focal points of the YAG and He-Ne beams is convenient and reliable with my optical system. This is done by axially adjusting expanders 27 and 37 and testing the results with photographic film until the focal point of the He-Ne beams is accurately coincident with the focal point of the YAG beam. Factory adjustment is reliable and easily maintained, partly because a unit of movement of one of the expanders 27 or 37 preferably produces only one-tenth unit of movement of the respective focal point.

My optical system also accommodates other combinations of visible light and surgical beam lasers producing substantially different wave lengths of light. Different wave lengths of radiation may require different coatings on mirror 50; but otherwise, the basic system is workable throughout a wide range of frequencies. My system can also be applied to various binocular microscopes, including microscopes arranged for operating table surgery.

I claim:

1. A surgical ophthalmic laser instrument including a binocular microscope, a surgical laser and visible light laser producing substantially different wave lengths of energy, and an optical system, said optical system comprising:
   a. a parallel plate beam splitter arranged for receiving a visible beam from said visible light laser;
   b. said parallel plate beam splitter having a half-reflective coating on one side and a full reflective coating on another side and being angled and arranged relative to said visible beam to divide said visible beam into a pair of equal and separated visible beams;
   c. an expander positioned in the path of said pair of visible beams for diverging said pair of visible beams;
   d. an expander positioned in the path of a surgical beam produced by said surgical laser for diverging said surgical beam;
   e. means for combining said diverging surgical beam and said diverging pair of visible beams on a coincident optical path;
   f. means for collimating light traveling on said coincident optical path;
   g. a mirror arranged on said coincident optical path between a binocular portion of said microscope and an objective portion of said microscope;
   h. said mirror having a first coating that reflects substantially all of said surgical beam and is substantially transparent to visible light;
   i. spaced-apart regions of said mirror having a second coating that reflects substantially all of both said pair of visible beams and said surgical beam; and
   j. said coatings and said mirror being arranged:
      (1) for directing said pair of visible beams and said surgical beam through said objective portion of said microscope to converge on the eye of a patient;
      (2) for transmitting visible light reflected from said patient's eye through said first coating to be visible with said binocular portion of said microscope; and
      (3) for not transmitting any surgical light through said mirror to said binocular portion of said microscope.

2. The optical system of claim 1 wherein said beam from said visible laser is polarized and incident on said parallel plate beam splitter at Brewster's angle.

3. The optical system of claim 2 wherein said visible beam is incident on an uncoated region of said parallel plate beam splitter, passes through said parallel plate beam splitter, and is incident on said half-reflective coating that divides said visible beam into said pair of equal beams, one of which passes through said half-reflective coating and the other of which reflects from said half-reflective coating, passes through said parallel plate beam splitter, and is reflected from said full reflective coating to emerge from said parallel plate beam splitter separated from the beam passing through said half-reflective coating.

4. The optical system of claim 1 including means for adjusting said expanders axially of said visible beams and said surgical beam for adjusting coincidence of the focal points of said visible beams and said surgical beam at the eye of the patient.

5. The optical system of claim 1 wherein said spaced-apart regions bearing said second coating are arranged at opposite top and bottom regions of said mirror.

6. The optical system of claim 1 wherein said surgical laser is a YAG laser and said visible light laser is a He-Ne laser.

7. The optical system of claim 1 wherein said first coating substantially covers said mirror, said second coating in said spaced-apart regions is superposed over said first coating and is up to about 500 angstrom units thick.

8. The optical system of claim 7 wherein said spaced-apart regions bearing said second coating are generally eliptical in shape and are arranged at opposite top and bottom regions of said mirror.

9. The optical system of claim 1 including an optical plate, means for mounting said visible laser, said surgical laser, said parallel plate beam splitter, said beam expanders, and said beam-combining means on said optical plate, and said optical plate being mounted on a movable support for said microscope so that said optical plate moves with said microscope.

10. The optical system of claim 9 including movable reflective means for directing said coincident optical path from said optical plate to said mirror.

11. The optical system of claim 9 wherein said beam from said visible laser is polarized and incident on said parallel plate beam splitter at Brewster's angle.

12. The optical system of claim 11 wherein said surgical laser is a YAG laser and said visible light laser is a He-Ne laser.

13. The optical system of claim 12 wherein a He-Ne beam from said He-Ne laser is incident on an uncoated region of said parallel plate beam splitter, passes through said parallel plate beam splitter, and is incident on said half-reflective coating that divides said He-Ne beam into said pair of equal beams, one of which passes through said half-reflective coating and the other of which reflects from said half-reflective coating, passes through said parallel plate beam splitter, and is reflected from said full reflective coating to emerge from said parallel plate beam splitter separated from the beam passing through said half-reflective coating.

14. The optical system of claim 13 including means for adjusting said expanders axially of said He-Ne beams and a beam from said YAG laser for adjusting coincidence of the focal points of said He-Ne beams and said YAG laser beam at the eye of the patient.

15. The optical system of claim 14 including movable reflective means for directing said coincident optical path from said optical plate to said mirror.

16. The optical system of claim 15 wherein said first coating substantially covers said mirror, said second coating in said spaced-apart regions is superposed over said first coating and is up to about 500 angstrom units thick.

17. The optical system of claim 16 wherein said spaced-apart regions bearing said second coating are generally eliptical in shape and are arranged at opposite top and bottom regions of said mirror.

* * * * *